(12) United States Patent
Sim (10) Patent No.: US 11,845,827 B2
(45) Date of Patent: Dec. 19, 2023

(54) PHOTOCURABLE COMPOSITION FOR 3D PRINTER FOR PRODUCING PATIENT-CUSTOMIZED CAST

(71) Applicant: GRAPHY INC., Seoul (KR)

(72) Inventor: Un Seob Sim, Seoul (KR)

(73) Assignee: GRAPHY INC., Seoul (KR)

( * ) Notice: Subject to any disclaimer, the term of this patent is extended or adjusted under 35 U.S.C. 154(b) by 702 days.

(21) Appl. No.: 17/053,311

(22) PCT Filed: Aug. 13, 2019

(86) PCT No.: PCT/KR2019/010331
§ 371 (c)(1),
(2) Date: Nov. 5, 2020

(87) PCT Pub. No.: WO2020/105843
PCT Pub. Date: May 28, 2020

(65) Prior Publication Data
US 2021/0070913 A1    Mar. 11, 2021

(30) Foreign Application Priority Data

Nov. 23, 2018  (KR) .................. 10-2018-0146099

(51) Int. Cl.
| | | |
|---|---|---|
| *C08G 18/08* | (2006.01) | |
| *B33Y 10/00* | (2015.01) | |
| *B33Y 70/00* | (2020.01) | |
| *B33Y 80/00* | (2015.01) | |
| *A61F 13/04* | (2006.01) | |
| *A61L 15/12* | (2006.01) | |
| *C08G 18/58* | (2006.01) | |
| *C08G 18/79* | (2006.01) | |
| *C08K 5/00* | (2006.01) | |
| *C08K 5/41* | (2006.01) | |
| *A61F 13/00* | (2006.01) | |

(52) U.S. Cl.
CPC .............. *C08G 18/08* (2013.01); *A61F 13/04* (2013.01); *A61L 15/12* (2013.01); *B33Y 10/00* (2014.12); *B33Y 70/00* (2014.12); *B33Y 80/00* (2014.12); *C08G 18/58* (2013.01); *C08G 18/79* (2013.01); *C08K 5/005* (2013.01); *C08K 5/41* (2013.01); *A61F 2013/00489* (2013.01); *A61F 2013/00621* (2013.01)

(58) Field of Classification Search
CPC ........ C08G 18/10; B33Y 10/00; B33Y 70/10; A61K 6/893; A61C 13/0019
See application file for complete search history.

(56) References Cited

U.S. PATENT DOCUMENTS

| | | | |
|---|---|---|---|
| 2016/0136889 A1* | 5/2016 | Rolland ..................... | C08J 5/00 264/1.27 |
| 2017/0342024 A1* | 11/2017 | Monnier ................ | C08F 22/22 |
| 2018/0126029 A1* | 5/2018 | Lomakin ................ | A61L 15/14 |

FOREIGN PATENT DOCUMENTS

| | | |
|---|---|---|
| CN | 101128223 A | 2/2008 |
| CN | 104334662 A | 2/2015 |
| CN | 107868443 A | 4/2018 |
| JP | 2018083901 A | 5/2018 |
| KR | 20110091742 A | 8/2011 |
| KR | 20170010299 A | 1/2017 |
| KR | 20180022452 A | 3/2018 |
| WO | WO2017172740 A1 | 10/2017 |

OTHER PUBLICATIONS

International Search Report of PCT/KR2019/010331, dated Nov. 15, 2019, English translation.
1 The extended European search report of EP19886523, dated Dec. 8, 2021.

* cited by examiner

*Primary Examiner* — Gregory Listvoyb
(74) *Attorney, Agent, or Firm* — STIP Law Group, LLC (57) ABSTRACT

The present disclosure relates to a photocurable composition for 3D printing for producing a patient-specific splint or cast. The photocurable composition easily produces a splint or cast conforming to the patient's body shape using 3D printing and makes it possible to adjust the immobilizing force of the splint or cast. In addition, the present disclosure provides a patient-specific splint or cast using a photocurable composition for 3D printing, which may produce a splint or cast, which may provide a necessary degree of compression by adjusting the immobilizing force thereof and is attachable and detectable as needed.

7 Claims, 4 Drawing Sheets

PHOTOCURABLE COMPOSITION FOR 3D PRINTER FOR PRODUCING PATIENT-CUSTOMIZED CAST

CROSS-REFERENCE TO RELATED APPLICATIONS

This application is the U.S. National Phase under 35 U.S.C. § 371 of International Application No. PCT/KR2019/010331 filed on Aug. 13, 2019, which in turn claims the benefit of Korean Application No. 10-2018-0146099 filed on Nov. 23, 2018, the disclosures of which are incorporated by reference into the present application.

TECHNICAL FIELD

The present disclosure relates to a photocurable composition for 3D printing for producing a patient-specific splint or cast, and more particularly, to a photocurable composition for 3D printing which can produce a splint or cast conforming to a patient's affected area through 3D information on the patient's affected area, in which the splint or cast can provide excellent immobilization by being produced using the photocurable composition for 3D printing.

BACKGROUND ART

In the musculoskeletal system consisting of bones, joints, muscles, tendons, ligaments, cartilage, nerves, etc., various diseases may be caused by various factors, including an external shock, excessive use, and incorrect posture. Representative orthopedic medical products used in the process of treating such diseases of the musculoskeletal system are a cast and a splint.

The cast is applied when it is necessary to immobilize the affected area for a certain period of time due to a fracture, ligament rupture, dislocation, or severe skin inflammation. The cast is shaped to completely cover the patient's affected area, mainly using a hydraulic plaster bandage or a thermosetting synthetic resin having a function similar thereto.

On the other hand, the splint is applied around the patient's affected area with a sprain, dislocation, a fracture, etc., and the affected area is immobilized by wrapping the outer circumference of the applied splint with a separate bandage.

The cast is used as a full cast, and the splint is used as a soft cast.

A typical conventional splint is made of a water-curable resin and used in the following manner. Before wetting with water, the splint is applied near the patient's affected area and roughly cut. The cut split is immersed in and taken out of water. The splint wet with water is applied to and hardened around the patient's affected area, and is fixed by wrapping the same with a separate bandage.

However, in the process of applying the conventional splint, a problem arises in that the patient's affected area is severely wet or by-products stick to the skin and the area surrounding the affected area is contaminated. In addition, problems arise in that, since the process of applying the splint is complicated, the frequency of continuously irritating the patient's affected area increases, and in that, in the process of molding while rubbing the splint to create an inner shape that is complementary to the patient's outer shape before the applied splint is completely hardened, a strong shock can also be applied to the patient.

In addition, a problem may arise in that the result of the application procedure differs depending on the ability of the surgeon. Specifically, in some cases, the compression strength is excessively strong, which causes problems such as blood circulation disorders in the patient, and in other cases, a problem arises in that the compression strength is so weak that the splint does not adequately support the patient's affected area but slips down.

As the material of the cast, plaster has been traditionally used, and synthetic resins such as plastic have recently been used.

The method of applying the cast generally includes wrapping the patient's affected area with a bandage and applying plaster thereto, or wrapping the patient's affected area with a plastic sheet. In the case of this conventional method, a problem may arise in that stronger compression than required may be applied to the patient's affected part, and on the contrary, proper immobilization is not achieved due to a procedure that does not meet the required compression.

Stronger compression than required leads to blood circulation disorders or damage to the nervous system in the patient, and weaker compression than required leads to skin damage due to continuous friction between the loose cast and the skin, or causes problems such as mis-resetting of bones.

In addition, since the period required to treat fractures, etc. is usually 3 to 5 weeks or more, a patient cannot wash his/her affected area compressed by the cast for a long period of time, and thus the affected area is exposed to the risk of various skin diseases caused by bacterial propagation. For this reason, the patient complains of extreme itching, and the cast contaminated by sweat and various foreign substances has a horrible stench, causing discomfort to not only the patient but also people around the patient.

Therefore, there is a need to develop a technology of producing a new type of patient-specific splint or cast using 3D printing technology, etc. after scanning the patient's affected area so as to solve the problems with the above-described conventional splint and cast, in which the produced splint or cast safely protects the patient's affected area and is configured that the immobilizing force thereof is easily adjusted.

PRIOR ART DOCUMENTS

Patent Documents (Patent Document 1) KR 10-2018-0022452 A1

DISCLOSURE

Technical Problem

An object of the present disclosure is to provide a photocurable composition for 3D printing for producing a patient-specific splint or cast.

Another object of the present disclosure is to provide a photocurable composition for 3D printing, which can easily produce a splint or cast conforming to the patient's body shape by 3D printing and enables the immobilizing force of the splint or cast to be easily adjusted.

Still another object of the present disclosure is to provide a patient-specific splint or cast using a photocurable composition for 3D printing which can produce a splint or cast, which can provide a necessary degree of compression by adjusting the immobilizing force thereof and can be attached and detached as needed.

Technical Solution

To achieve the above objects, a photocurable composition for 3D printing for producing a patient-specific splint or cast according to an embodiment of the present disclosure is a photocurable composition for producing a patient-specific splint or cast using 3D printing, and includes: a UV-curable polyurethane oligomer represented by the following Formula 1; a photoinitiator; a silane coupling agent; an oligomer; and a stabilizer, wherein the patient-specific splint or cast has a tensile strength of 50 to 60 N/m² and a flexural strength of 60 to 75 N/m²:

substituted heteroarylamino group, the substituted alkylsilyl group, the substituted arylsilyl group and the substituted aryloxy group are substituted with one or more substituents selected from the group consisting of hydrogen, deuterium, a cyano group, a nitro group, a halogen group, a hydroxyl group, an alkyl group having 1 to 30 carbon atoms, a cycloalkyl group having 1 to 20 carbon atoms, an alkenyl group having 2 to 30 carbon atoms, an alkynyl group having

[Formula 1]

[Formula 2]

wherein

A and A' are each a substituent represented by Formula 2 above;

n, m, o, p, q and r are the same or different and are each independently an integer ranging from 1 to 100;

$L_1$ and $L_2$ are the same or different and are each independently a substituted or unsubstituted alkylene group having 1 to 200 carbon atoms, a substituted or unsubstituted arylene group having 6 to 200 carbon atoms, a substituted or unsubstituted heteroarylene group having 5 to 200 nuclear atoms, or a substituted or unsubstituted cycloalkylene group having 3 to 200 carbon atoms;

$R_1$ to $R_8$ are the same or different and are each independently selected from the group consisting of hydrogen, deuterium, a cyano group, a nitro group, a halogen group, a hydroxyl group, a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 carbon atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl group having 6 to 30 carbon atoms, and a substituted or unsubstituted aryloxy group having 6 to 30 carbon atoms;

the substituted alkylene group, the substituted arylene group, the substituted heteroarylene group, the substituted cycloalkylene group, the substituted alkyl group, the substituted cycloalkyl group, the substituted alkenyl group, the substituted alkynyl group, the substituted aralkyl group, the substituted aryl group, the substituted heteroaryl group, the substituted heteroarylalkyl group, the substituted alkoxy group, the substituted alkylamino group, the substituted arylamino group, the substituted aralkylamino group, the 2 to 24 carbon atoms, an aralkyl group having 7 to 30 carbon atoms, an aryl group having 6 to 30 carbon atoms, a heteroaryl group having 5 to 60 nuclear atoms, a heteroarylalkyl group having 6 to 30 carbon atoms, an alkoxy group having 1 to 30 carbon atoms, an alkyl amino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms, and an aryloxy group having 6 to 30 carbon atoms, and when they are substituted with a plurality of substituents, these substituents are the same or different.

The UV-curable polyurethane oligomer has a weight-average molecular weight of 10,000 to 1,000,000.

The photoinitiator is a compound represented by the following Formula 3:

[Formula 3]

wherein $X_1$ is S, O or N($R_{11}$);

$R_9$ to $R_{11}$ are the same or different and are each independently hydrogen, deuterium, a cyano group, a nitro group, a halogen group, a hydroxyl group, a substituted or unsubstituted alkyl group having 1 to 30 carbon atoms, or a substituted or unsubstituted cycloalkyl group having 3 to 30 carbon atoms; and the substituted alkyl group and the substituted cycloalkyl group are substituted with one or more substituents selected from the group consisting of hydrogen, deuterium, a cyano group, a nitro group, a halogen group, a hydroxyl group, an alkyl group having 1 to 30 carbon atoms, a cycloalkyl group having 1 to 20 carbon atoms, an alkenyl group having 2 to 30 carbon atoms, an alkynyl group having 2 to 24 carbon atoms, an aralkyl group having 7 to 30 carbon atoms, an aryl group having 6 to 30 carbon atoms, a heteroaryl group having 5 to 60 nuclear atoms, a heteroarylalkyl group having 6 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms, and an aryloxy group having 6 to 30 carbon atoms, and when they are substituted with a plurality of substituents, these substituents are the same or different.

The oligomer may be selected from the group consisting of an epoxy acrylate oligomer, $H_{12}$ Dian-bis-glycidyl ether (4,4'-(1-methylethylidene)biscyclohexanol polymer with (chloromethyl)oxirane), and a mixture thereof.

The stabilizer may be selected from the group consisting of 2,6-di-tert-butyl-p-cresol, diethylethanolamine, trihexylamine, a hindered amine, an organic phosphate, a hindered phenol, and mixtures thereof.

An implant is additionally formed in the patient-specific splint or cast in order to prevent the splint or cast from loosening due to changes in the state of the patient's affected area and maintain the ability of the splint or cast to support the patient's affected area.

The patient-specific splint or cast produced using 3D printing according to an embodiment of the present disclosure may include the photocurable composition for 3D printing.

Hereinafter, the present disclosure will be described in more detail.

3D printing in the present disclosure refers to a process of producing a three-dimensional object by depositing a material using 3D digital data. In the present specification, description is made focusing on digital light processing (DLP) technology, Stereolithography apparatus (SLA) technology and PolyJet technology as 3D printing technologies, but it may be understood that the present disclosure may also be applied to other 3D printing technologies.

The photocurable composition in the present disclosure is a material that is cured by light irradiation, and refers to a polymer that is crosslinked and polymerized into a polymer network. In the present specification, description is made focusing on UV light, but the present disclosure is not limited to UV light and may also be applied to other light.

The photocurable composition for 3D printing for producing a patient-specific splint or cast according to an embodiment of the present disclosure is a photocurable composition for producing a patient-specific splint or cast using 3D printing, and includes: a UV-curable polyurethane oligomer represented by the following Formula 1; a photoinitiator; a silane coupling agent; an oligomer; and a stabilizer, wherein the patient-specific splint or cast has a tensile strength of 50 to 60 N/m² and a flexural strength of 60 to 75 N/m²:

$L_1$ and $L_2$ are the same or different and are each independently a substituted or unsubstituted alkylene group having 1 to 200 carbon atoms, a substituted or unsubstituted arylene group having 6 to 200 carbon atoms, a substituted or unsubstituted heteroarylene group having 5 to 200 nuclear atoms, or a substituted or unsubstituted cycloalkylene group having 3 to 200 carbon atoms;

$R_1$ to $R_8$ are the same or different and are each independently selected from the group consisting of hydrogen, deuterium, a cyano group, a nitro group, a halogen group, a hydroxyl group, a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 carbon atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl group having 6 to 30 carbon atoms, and a substituted or unsubstituted aryloxy group having 6 to 30 carbon atoms;

the substituted alkylene group, the substituted arylene group, the substituted heteroarylene group, the substituted cycloalkylene group, the substituted alkyl group, the substituted cycloalkyl group, the substituted alkenyl group, the substituted alkynyl group, the substituted aralkyl group, the substituted aryl group, the substituted heteroaryl group, the substituted heteroarylalkyl group, the substituted alkoxy group, the substituted alkylamino group, the substituted arylamino group, the substituted aralkylamino group, the substituted heteroarylamino group, the substituted alkylsilyl group, the substituted arylsilyl group and the substituted aryloxy group are substituted with one or more substituents selected from the group consisting of hydrogen, deuterium, a cyano group, a nitro group, a halogen group, a hydroxyl group, an alkyl group having 1 to 30 carbon atoms, a cycloalkyl group having 1 to 20 carbon atoms, an alkenyl group having 2 to 30 carbon atoms, an alkynyl group having 2 to 24 carbon atoms, an aralkyl group having 7 to 30 carbon

[Formula 1]

[Formula 2]

wherein

A and A' are each a substituent represented by Formula 2 above;

n, m, o, p, q and r are the same or different and are each independently an integer ranging from 1 to 100;

atoms, an aryl group having 6 to 30 carbon atoms, a heteroaryl group having 5 to 60 nuclear atoms, a heteroarylalkyl group having 6 to 30 carbon atoms, an alkoxy group having 1 to 30 carbon atoms, an alkyl amino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms, and an aryloxy group having 6 to 30 carbon atoms, and when they are substituted with a plurality of substituents, these substituents are the same or different.

The UV-curable polyurethane oligomer is a polymer having a weight-average molecular weight of 10,000 to 1,000,000.

More preferably, the UV-curable polyurethane oligomer is a compound represented by the following Formula 4:

[Formula 4]

wherein

A and A' are as defined in Formula 1 above;

n', m', o', p', q' and r' are the same or different and are each independently an integer ranging from 1 to 100; and $R_{12}$ and $R_{13}$ are the same or different and are each independently selected from the group consisting of an alkylsilyl group having 1 to 30 carbon atoms, an arylsilyl group having 6 to 30 carbon atoms, an alkoxy group having 1 to 30 carbon atoms, and a cycloalkyl group having 1 to 20 carbon atoms.

More specifically, the UV-curable polyurethane oligomer is a polymer compound having a photocurable functional group for UV curing linked to a polyurethane oligomer, and the photocurable functional group is the substituent represented by Formula 2 above.

The substituent represented by Formula 2 contains a carbon-carbon double bond therein, and may exhibit photocuring activity by the carbon-carbon double bond.

In addition, the UV-curable polyurethane oligomer includes a polyurethane structure as a main chain, and the photocurable functional group is linked to the polyurethane structure. Linkage between the polyurethane structure and the photocurable functional group is achieved using a linker including a soft functional group attached to a urethane linker and a linker including a hard functional group attached to a urethane linker.

The linker including a soft functional group attached to a urethane linker makes it possible to use the flexible property of the soft functional group, and the hard functional group may exhibit heat resistance.

That is, as the photocurable functional group is linked to the UV-curable polyurethane oligomer and the linker includes the soft functional group and the hard functional group, the UV-curable polyurethane oligomer may exhibit a flexible effect using a carbon skeleton having soft properties at room temperature, and may also exhibit strong heat resistance using a carbon skeleton having hard properties at room temperature.

As the UV-curable polyurethane oligomer includes the carbon skeleton having hard properties, it is possible to produce a 3D printed product having excellent physical properties such as thermal properties, strength, elastic modulus and tensile elongation.

In addition, as the UV-curable polyurethane oligomer includes the carbon skeleton having soft properties, it is possible to produce a 3D printed product which, even when the original shape thereof is deformed during use, may be restored to the original shape thereof.

In general, a composition for 3D printing may include only a carbon skeleton having hard properties in order to improve the physical properties of a 3D printed product. However, in this case, a problem arises in that, when the shape of the 3D printed product is deformed during use, the 3D printed product cannot be restored to the original shape, and thus cannot be used multiple times.

As the composition for 3D printing according to the present disclosure includes a carbon skeleton having hard properties and a carbon skeleton having soft properties in the UV-curable polyurethane oligomer, the 3D printed product produced from the composition may exhibit excellent physical properties such as thermal properties, strength, elastic modulus and tensile elongation, and may also use the flexible property of the soft functional group, and thus when the shape thereof is deformed during use, the printed product may be restored to the original shape thereof and reused.

In general, plaster that is used as a material for a splint or cast is not deformable, and a plastic material for a splint or cast may be deformed partially or broken due to a strong external force.

That is, the splint or cast should have excellent physical properties in order to maintain immobilization as the splint or cast. However, in the case in which the splint or cast only has excellent physical properties, a problem arises in that the splint or cast is damaged by an external force or when the shape thereof is deformed, the splint or cast cannot be restored to the original shape thereof.

As the photocurable composition for a splint or cast according to the present disclosure uses the UV-curable polyurethane polymer including a carbon skeleton having soft properties and a carbon skeleton having hard properties, a splint or cast produced using the composition exhibits physical properties for maintaining immobilization by the carbon skeleton having hard properties. At the same time, as the composition also includes the carbon skeleton having soft properties, when the shape of the splint or cast is deformed during use, the splint or cast may be restored to the original shape thereof, and may exhibit excellent thermal properties, strength, elastic modulus and tensile elongation.

The present disclosure provides a photocurable composition for 3D printing which can produce a splint or cast, which can provide a necessary degree of compression by adjusting the immobilizing force thereof and can be attached or detached as needed.

In the case of a plaster or plastic material that has been used as a conventional splint or cast material, adjustment of the immobilizing force is unnecessary or attachment or detachment is not considered, and thus whether or not the plaster or plastic material has excellent physical properties corresponds to the most important factor that influences the use of plaster or plastic material as a splint or cast material.

However, in the case of a conventional splint or cast material, when stronger compression than necessary is applied, it causes pain to the patient, and in this case, there is an inconvenience in that the splint or cast should be dismantled and a splint or cast should be produced again according to the shape of the patient's affected area.

On the other hand, according to the present disclosure, 3D printing is used, and thus it is possible to produce a splint or cast that almost matches the shape of the patient's affected area, unlike the case in which a conventional splint or cast is produced. In addition, when the shape of the affected area is deformed with the passage of time, the shape of the splint or cast can be adjusted using the soft properties of the splint or cast material in order to increase the immobilizing force. Alternatively, an implant may be formed in the splint or cast in order to prevent the splint or cast from loosening and maintain the ability of the splint or cast to support the affected area.

In order to adjust the shape of the splint or cast, the upper and lower portions thereof are printed separately during production of the splint or cast, and holes are formed in the adhering surfaces of the upper and lower portions so that a string such as a wire can be connected thereto. When the splint or cast becomes loose due to deformation of the affected area, a string such as a wire may be connected to the holes to prevent the splint or cast from loosening and maintain the ability of the splint or cast to support the affected area.

That is, since the splint or cast produced using the photocurable composition of the present disclosure has soft properties, holes may be formed therein and a string may be connected thereto, thereby preventing the splint or cast from loosening and maintaining the ability of the splint or cast to support the affected area. In other words, if a splint or cast has only hard properties and thus has excellent physical properties, but has no soft properties, when the splint or cast is tightened using a string such as a wire, the shape thereof is difficult to deform, and when a greater external force is applied to deform the shape thereof, the splint or cast may be broken.

More specifically, the use of the composition for 3D printing according to the present disclosure may provide a patient-specific splint or cast having excellent properties, such as a tensile modulus of 1,500 to 2,500 MPa, a flexural modulus of 1,000 to 3,500 MPa, and a tensile strength of 45 to 90 MPa.

The photoinitiator is a compound represented by the following Formula 3:

[Formula 3]

wherein

$X_1$ is S, O or $N(R_{11})$;

$R_9$ to $R_{11}$ are the same or different and are each independently hydrogen, deuterium, a cyano group, a nitro group, a halogen group, a hydroxyl group, a substituted or unsubstituted alkyl group having 1 to 30 carbon atoms, or a substituted or unsubstituted cycloalkyl group having 3 to 30 carbon atoms; and the substituted alkyl group and the substituted cycloalkyl group are substituted with one or more substituents selected from the group consisting of hydrogen, deuterium, a cyano group, a nitro group, a halogen group, a hydroxyl group, an alkyl group having 1 to 30 carbon atoms, a cycloalkyl group having 1 to 20 carbon atoms, an alkenyl group having 2 to 30 carbon atoms, an alkynyl group having 2 to 24 carbon atoms, an aralkyl group having 7 to 30 carbon atoms, an aryl group having 6 to 30 carbon atoms, a heteroaryl group having 5 to 60 nuclear atoms, a heteroarylalkyl group having 6 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms, and an aryloxy group having 6 to 30 carbon atoms, and when they are substituted with a plurality of substituents, these substituents are the same or different.

More preferably, the photoinitiator is a compound represented by the following Formula 5:

[Formula 5]

The oligomer may be selected from the group consisting of an epoxy acrylate oligomer, $H_{12}$ Dian-bis-glycidyl ether (4,4'-(1-methylethylidene)biscyclohexanol polymer with (chloromethyl)oxirane), and a mixture thereof.

More specifically, the epoxy acrylate oligomer may be one or more compound selected from the group consisting of a phenyl epoxy (meth)acrylate oligomer, a bisphenol A epoxy di(meth)acrylate oligomer, an aliphatic alkyl epoxy di(meth)acrylate oligomer, and an aliphatic alkyl epoxy tri(meth)acrylate oligomer. The oligomer may reduce swelling caused by an organic solvent, and may also improve surface hardness, abrasion resistance, heat resistance, and the like.

More specifically, the silane coupling agent is 3-methacryloxypropyltrimethoxysilane, but is not limited thereto.

The stabilizer is selected from the group consisting of 2,6-di-tert-butyl-p-cresol, diethylethanolamine, trihexylamine, a hindered amine, an organic phosphate, a hindered phenol, and mixtures thereof. More specifically, the stabilizer is 2,6-di-tert-butyl-p-cresol.

To improve thermal and oxidation stability, storage stability, flow properties and process properties, conventional additives may be added, such as a leveling agent, a slip agent or a stabilizer.

The photocurable composition for 3D printing for producing a splinter or cast include the UV-curable polyurethane oligomer and may include, based on 100 parts by weight of the UV-curable polyurethane oligomer, 1.5 to 15 parts by weight of the photoinitiator, 0.1 to 1.5 parts by weight of the silane coupling agent, 50 to 80 parts by weight of the oligomer, and 0.1 to 2 parts by weight of the stabilizer. When the silane coupling agent is used in an amount within the above-described range, it may improve compatibility with and adhesion to the resin when used for surface treatment of a pigment or a filler. If the oligomer is used in an amount exceeding the upper limit of the above-described range, it may reduce the mold release property of the resin by increasing surface energy and degrade the surface properties of the mold, such as post-stamping restoration force, by increasing surface hardness. When the stabilizer is used in an amount within the above-described range, it may reduce ambient cure and increase strength.

When the composition is used for a splint or cast, the content of the oligomer in the composition is increased to enhance physical properties. In particular, as the oligomer for enhancing physical properties, an oligomer represented by the following Formula 6 may be used:

[Formula 6]

As the oligomer represented by Formula 6 above includes a hard carbon-carbon bond, it may enhance the physical properties of a splint or cast produced using the photocurable composition including the oligomer.

The production of a splint or cast according to the present disclosure may be performed using Korean Patent No. 10-1820674 B1, entitled "Digital Printing Apparatus and Method for Printing Splint or Cast Using 3D Information".

More specifically, the method includes: a 3D input step of inputting 3D information on a patient's affected area; a 3D model generation step of generating a plurality of 3D models divided into a plurality of regions by setting a range of interest using the 3D information and setting the central axis of the tooth structure as the x-axis; and a 3D printing step of printing the plurality of 3D models by a digital light processing (DLP) method.

A 3D printing unit prints the plurality of 3D models by the digital light processing (DLP) method. The 3D printing unit can generate an entire calibration device in a short time by printing the 3D models at the same time or different times. The 3D printing unit may print a patient-specific sprint or cast using the photocurable composition for 3D printing of the present disclosure by user's setting.

Figure 1:
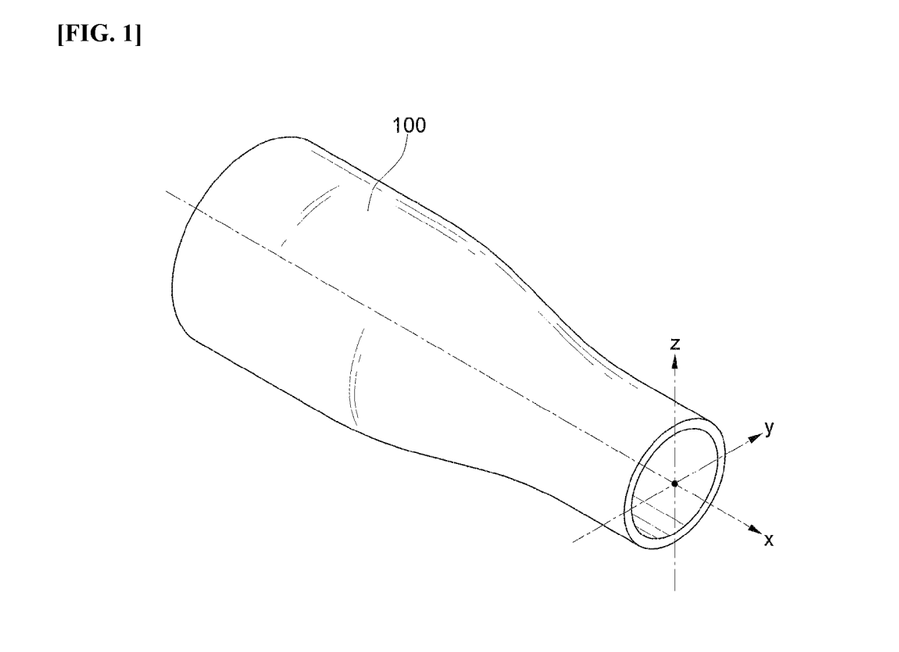
FIG. 1 is a view illustrating a patient-specific splint or cast formed by a digital printing apparatus for printing a splint or cast using 3D information according to an embodiment of the present disclosure.

More specifically, 3D models that are generated through the digital printing apparatus for printing a splint or cast using 3D information are formed using the central axis of the through direction of the splint or cast as the x-axis. In this case, as shown in FIG. 1, the x-axis and the y-axis are set as a first boundary 111, and a 3D model 100 is divided into the upper and lower portions while being divided by the xy plane, thereby forming a first model 110. In this case, the first boundary 111 may also be subjected to UV treatment or heat treatment to facilitate bonding at the boundary. In addition, an open/close range 101 may be set at one side of the first model 110, and 3D printing may be performed in a state in which the open/close range 101 is empty.

Figure 2:
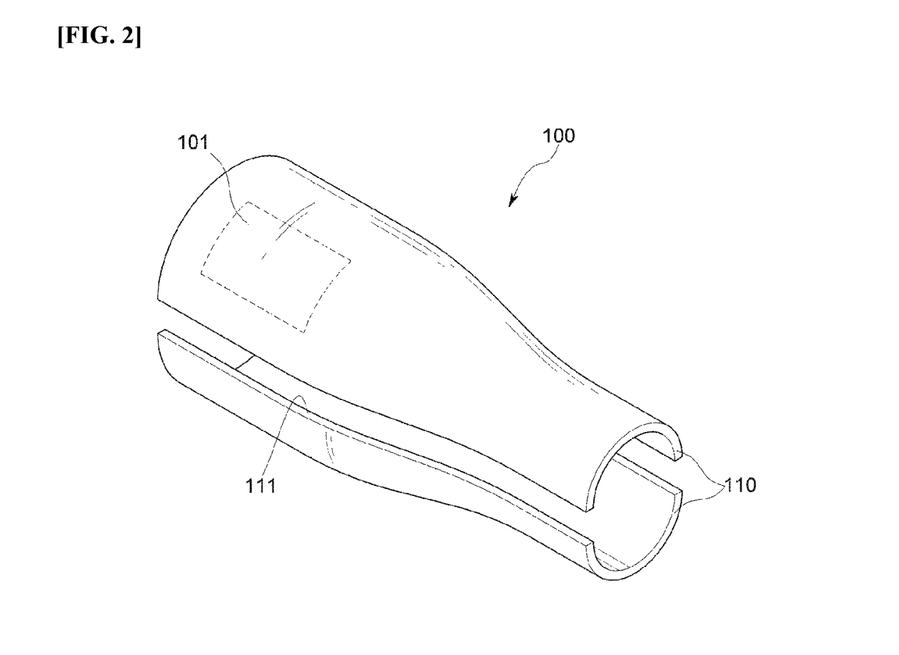
FIG. 2 is a view illustrating that a first model is formed by division of a 3D model according to an embodiment of the present disclosure.

In addition, as shown in FIG. 2, the y-axis and the z-axis are set as a second boundary 121, and a 3D model 300 is divided into sections while being divided by the yz plane, thereby forming a second model 120. Therefore, it is possible to increase the production speed by separately printing the upper and lower portions of the digital splint or cast for each section. In this case, the second boundary 121 may also be subjected to UV photocuring or heat treatment to facilitate bonding at the boundary. In addition, an open/close range 301 may be set at one side of the second model 120, and 3D printing may be performed in a state in which the open/close range 301 is empty.

Figure 3:
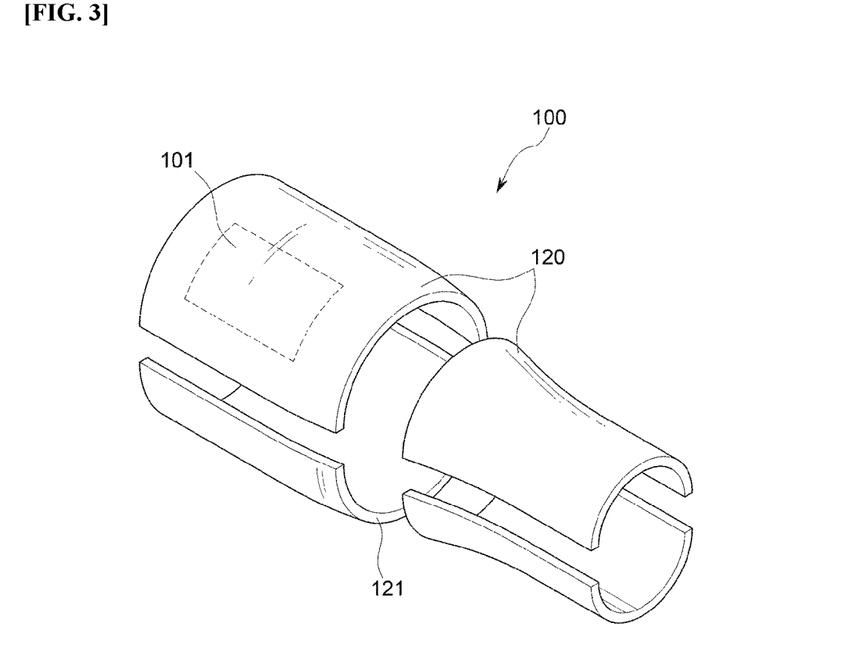
FIG. 3 is a view illustrating that a second model is formed by division of a 3D model according to an embodiment of the present disclosure.

FIG. 3 is a view illustrating an implant model that is added to the 3D model according to FIG. 3.

Referring to FIG. 3, an implant that is added to the 3D model 100 may be formed. An implant model 200 may be formed using a difference between 3D information on the patient's affected area acquired at the first time point and 3D information on the patient's affected area acquired at the second time point. The implant model 200 is formed to be coupled to the inside of the 3D model 100.

Accordingly, the implant model 200 may prevent the splint or cast from loosening due to changes in the state of the patient's affected area and support the affected area more firmly. In addition, protrusions 201 may be formed on the inner or outer surface of the implant model 200, so that a gap may be provided between the existing 3D model 100 and the skin to ensure air ventilation.

Figure 4:
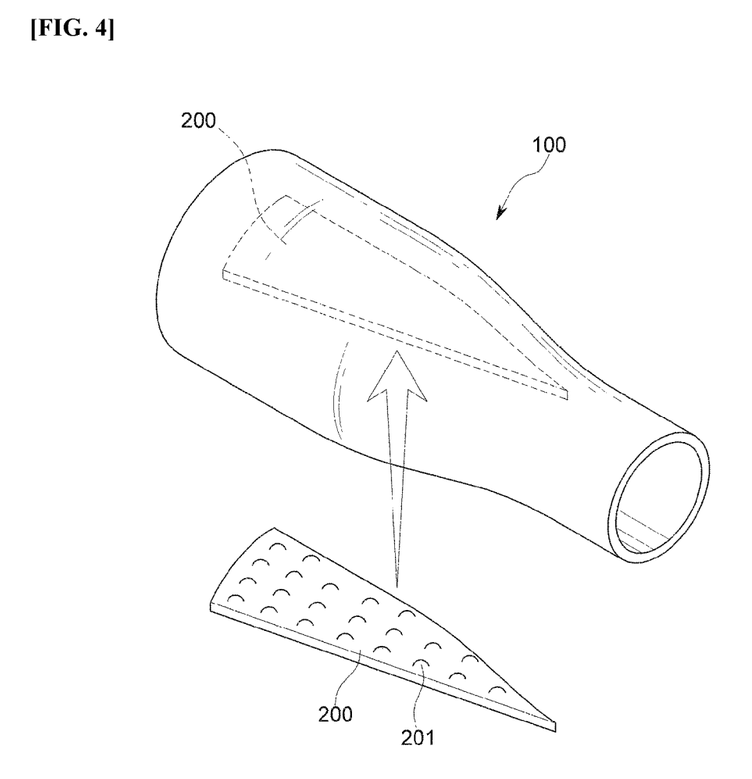
FIG. 4 is a view illustrating an implant model that is added into a 3D model according to an embodiment of the present disclosure.

FIG. 4 is a view illustrating an implant model that is added to the 3D model. Referring to FIG. 4, the implant model 200 may be formed using a difference between 3D information on the patient's affected area acquired at the first time point and 3D information on the patient's affected area acquired at the second time point. The implant model 200 is formed to be coupled to the inside of the 3D model 100. Accordingly, the implant model 200 may prevent the splint or cast from loosening due to changes in the state of the patient's affected area and support the affected area more firmly. In addition, protrusions 201 may be formed on the inner or outer surface of the implant model 200, so that a gap may be provided between the existing 3D model 100 and the skin to ensure air ventilation.

Figure 5:
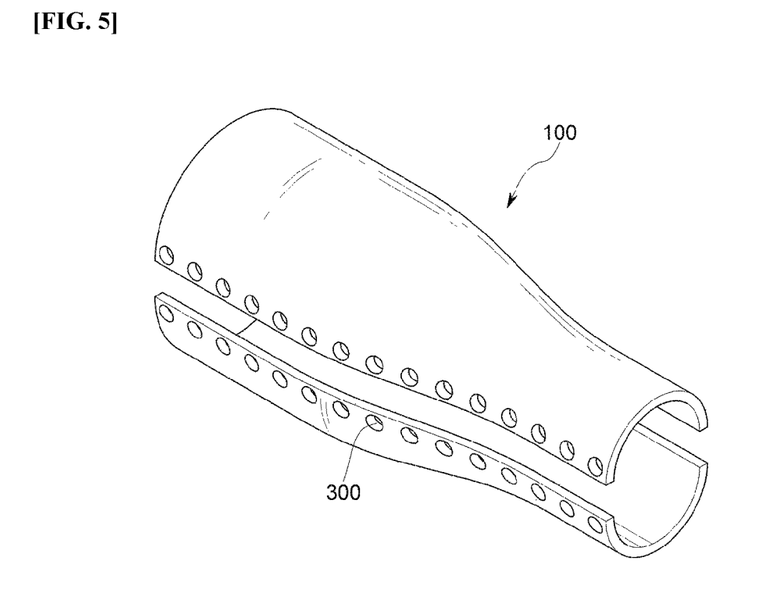
FIG. 5 is a view illustrating a model in which holes are formed at both sides of the boundary in a 3D model according to an embodiment of the present disclosure.
Figure 6:
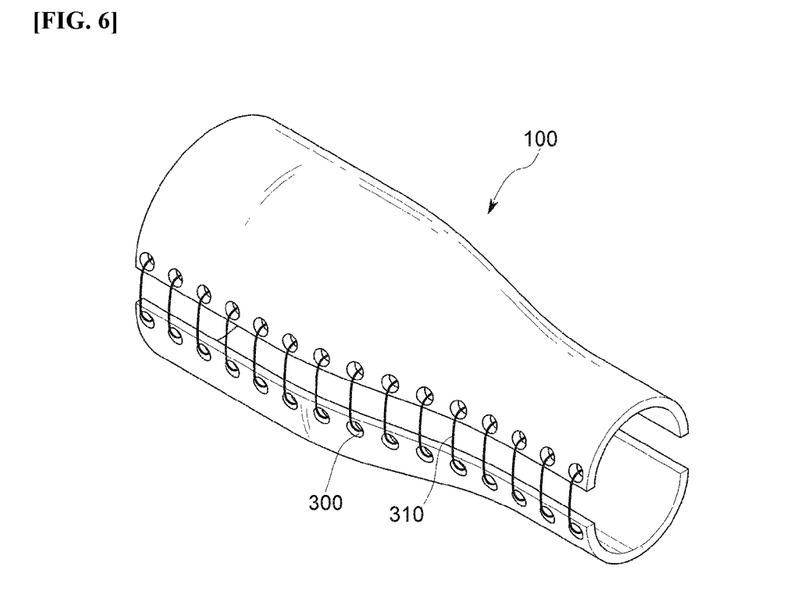
FIG. 6 is a view illustrating a model in which holes are formed at both sides of the boundary in a 3D model according to an embodiment of the present disclosure.

FIG. 5 shows that holes are formed symmetrically with respect to the first boundary 111 of the 3D model 110. A wire may be connected between the symmetrical holes. FIG. 6 shows that a wire is connected to the holes formed symmetrically with respect to the first boundary 111.

Referring to FIGS. 5 and 6, as shown in FIG. 4, the splint or cast may become loose due to changes in the state of the affected area. At this time, an internal implant may be additionally formed in the splint or cast and may prevent loosening of the splint or cast. However, in order to use the internal implant, 3D information on the patient's affected area at the second time point needs to be used, and thus additional information on the patient's affected area is required, which may cause a cumbersome problem.

In order to prevent this problem, as shown in FIGS. 5 and 6, holes may be formed symmetrically with respect to the first boundary 111, and a loose splint or cast may be tightened using the wire connected to the holes, thereby maintaining immobilization with the splint or cast.

Advantageous Effects

The present disclosure provides a photocurable composition for 3D printing, which can easily produce a splint or cast conforming to the patient's body shape using 3D printing and makes it possible to adjust the immobilizing force of the splint or cast.

In addition, the present disclosure provides a patient-specific splint or cast using a photocurable composition for 3D printing which can a splint or cast, which can provide a necessary degree of compression by adjusting the immobilizing force thereof and is attachable and detachable as needed.

BEST MODE

The present disclosure is directed to a photocurable composition for producing a patient-specific splint or cast using 3D printing, the photocurable composition including: a UV-curable polyurethane oligomer represented by the following Formula 1; a photoinitiator; a silane coupling agent; an oligomer; and a stabilizer, wherein the patient-specific splint or cast has a tensile strength of 50 to 60 N/m$^2$ and a flexural strength of 60 to 75 N/m$^2$:

having 7 to 30 carbon atoms, a substituted or unsubstituted aryl group having 6 to 30 carbon atoms, a substituted or unsubstituted heteroaryl group having 5 to 60 carbon atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl group having 6 to 30 carbon atoms, and a substituted or unsubstituted aryloxy group having 6 to 30 carbon atoms;

the substituted alkylene group, the substituted arylene group, the substituted heteroarylene group, the substituted cycloalkylene group, the substituted alkyl group, the substituted cycloalkyl group, the substituted alkenyl group, the substituted alkynyl group, the substituted aralkyl group, the substituted aryl group, the substituted heteroaryl group, the substituted heteroarylalkyl group, the substituted alkoxy group, the substituted alkylamino group, the substituted arylamino group, the substituted aralkylamino group, the substituted heteroarylamino group, the substituted alkylsilyl group, the substituted arylsilyl group and the substituted aryloxy group are substituted with one or more substituents selected from the group consisting of hydrogen, deuterium, a cyano group, a nitro group, a halogen group, a hydroxyl group, an alkyl group having 1 to 30 carbon atoms, a cycloalkyl group having 1 to 20 carbon atoms, an alkenyl

[Formula 1]

[Formula 2]

wherein

A and A' are each a substituent represented by Formula 2 above;

n, m, o, p, q and r are the same or different and are each independently an integer ranging from 1 to 100;

$L_1$ and $L_2$ are the same or different and are each independently a substituted or unsubstituted alkylene group having 1 to 200 carbon atoms, a substituted or unsubstituted arylene group having 6 to 200 carbon atoms, a substituted or unsubstituted heteroarylene group having 5 to 200 nuclear atoms, or a substituted or unsubstituted cycloalkylene group having 3 to 200 carbon atoms;

$R_1$ to $R_8$ are the same or different and are each independently selected from the group consisting of hydrogen, deuterium, a cyano group, a nitro group, a halogen group, a hydroxyl group, a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group group having 2 to 30 carbon atoms, an alkynyl group having 2 to 24 carbon atoms, an aralkyl group having 7 to 30 carbon atoms, an aryl group having 6 to 30 carbon atoms, a heteroaryl group having 5 to 60 nuclear atoms, a heteroarylalkyl group having 6 to 30 carbon atoms, an alkoxy group having 1 to 30 carbon atoms, an alkyl amino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms, and an aryloxy group having 6 to 30 carbon atoms, and when they are substituted with a plurality of substituents, these substituents are the same or different.

MODE FOR INVENTION

Hereinafter, embodiments of the present disclosure will be described in detail so that those skilled in the art to which the present disclosure pertains can easily carry out the present disclosure. However, the present disclosure may be embodied in a variety of different forms and is not limited to the embodiments described herein.

Preparation Example: Preparation of Photocurable Polymer Composition for 3D Printing Photocurable polymer compositions for 3D printing were prepared by mixing a UV-curable polyurethane oligomer represented by the following Formula 7 or 8, a photoinitiator represented by the following Formula 5, 3-methacryloxy-propyltrimethoxysilane, an epoxy acrylate oligomer represented by the following Formula 6, and 2,6-di-tert-butyl-p-cresol. The oligomer and the like, used in the preparation of the polymer compositions, were purchased, and the contents of the components are shown in Table 1 below.

wherein

A and A' are each a substituent represented by Formula 2 above, and n', m', o', p', q' and r' are the same or different and are each independently an integer ranging from 1 to 100.

TABLE 1

|  | G10 | G20 | G30 | G40 | G50 | G60 | G70 | G80 |
|---|---|---|---|---|---|---|---|---|
| Formula 7 | 100 | 100 | 100 | 100 | 100 | 100 | — | — |
| Formula 8 | — | — | — | — | — | — | 100 | 100 |
| Photoinitiator | 1 | 1.5 | 5 | 10 | 15 | 20 | 10 | 15 |
| Silane coupling agent | 0.05 | 0.1 | 0.5 | 1 | 1.5 | 2 | 1 | 1.5 |

[Formula 7]

[Formula 8]

[Formula 2]

[Formula 5]

[Formula 6]

TABLE 1-continued

|  | G10 | G20 | G30 | G40 | G50 | G60 | G70 | G80 |
|---|---|---|---|---|---|---|---|---|
| Oligomer | 10 | 50 | 60 | 70 | 80 | 90 | 70 | 80 |
| Stabilizer | 0.05 | 0.1 | 0.5 | 1 | 2 | 3 | 1 | 2 |

(unit: parts by weight)

Test Example: Test for Evaluation of Physical Properties

1. Test conditions
1-1. Tensile test
Test method: ASTM D638
Testing instrument: Universal Testing Machine
Test speed: 50 mm/min
Distance between grips: 115 mm
Load cell: 3000 N
Elasticity range: (0.05 to 0.25)%
Yield point: 0.2% offset
Test environment: (23±2°) C. and (50±5)% R.H.
1-2. Flexural test
Test method: ASTM D790
Testing instrument: Universal Testing Machine
Test speed: 1.4 mm/min
Distance between spans: 55 mm
Load cell: 200 N
Elasticity range: (0.05 to 0.25)%
Test environment: (23±2°) C. and (50±5)% R.H.
2. Test results
The above tests were conducted by the Korea Polymer Testing & Research Institute. The specimens provided were obtained from the polymer compositions of S10 to S80 in Table 1 above by printing using a 3D printer.
The results of the tensile test are shown in Table 2 below.

TABLE 2

|  | S10 | S20 | S30 | S40 | S50 | S60 | S70 | S80 |
|---|---|---|---|---|---|---|---|---|
| Maximum load (N) | 1659.23 | 1752.34 | 1955.11 | 2224.92 | 2234.82 | 1827.21 | 2251.64 | 2244.52 |
| Tensile strength (N/m$^2$) | 46.21 | 50.12 | 51.14 | 55.38 | 56.24 | 47.58 | 57.25 | 58.62 |
| Yield strength (N/m$^2$) | 46.55 | 50.10 | 50.59 | 54.28 | 55.89 | 48.21 | 56.54 | 58.42 |
| Elongation (%) | 35.98 | 38.10 | 38.89 | 39.85 | 40.23 | 37.12 | 40.69 | 42.34 |
| Elastic modulus (N/m$^2$) | 1498.23 | 1645.54 | 1688.54 | 1721.32 | 1722.25 | 1521.54 | 1744.35 | 1746.24 |

The results of the flexural test are shown in Table 3 below.

TABLE 3

|  | S10 | S20 | S30 | S40 | S50 | S60 | S70 | S80 |
|---|---|---|---|---|---|---|---|---|
| Maximum load (N) | 94.1 | 95.4 | 96.1 | 96.3 | 97.1 | 95.2 | 98.4 | 98.6 |
| Flexural strength (N/m$^2$) | 48.4 | 60.1 | 64.2 | 69.3 | 70.2 | 58.1 | 72.8 | 74.2 |
| Strain (%) | 10.12 | 12.98 | 12.95 | 13.04 | 13.25 | 11.75 | 14.11 | 14.52 |
| Elastic modulus (N/m$^2$) | 1109.14 | 1204.72 | 1214.46 | 1215.72 | 1227.43 | 1201.58 | 1241.14 | 1282.43 |

From the tensile test and flexural test results in Tables 2 and 3 above, it was confirmed that the photocurable compositions of the present disclosure exhibited excellent tensile strength, flexural strength, elastic modulus, yield strength, elongation and strain.

Although the preferred embodiments of the present disclosure have been described above in detail, the scope of the present disclosure is not limited thereto. Various modifications and improvements, which are made by those skilled in the art without departing from the basic concept of the present disclosure as defined in the appended claims, also fall within the scope of the present disclosure.

INDUSTRIAL APPLICABILITY

The present disclosure relates to a photocurable composition for 3D printing for producing a patient-specific splint or cast, and more particularly, to a photocurable composition for 3D printing which can produce a splint or cast conforming to a patient's affected area through 3D information on the patient's affected area, in which the splint or cast can provide excellent immobilization by being produced using the photocurable composition for 3D printing.

The invention claimed is:

1. A photocurable composition for 3D printing for producing a patient-specific splint or cast using 3D printing, the composition comprising: a UV-curable polyurethane oligomer represented by the following Formula 1; a photoinitiator; a silane coupling agent; an oligomer; and a stabilizer, wherein the patient-specific splint or cast has a tensile strength of 50 to 60 N/m$^2$ and a flexural strength of 60 to 75 N/m$^2$:

[Formula 1]

[Formula 2]

wherein

A and A' are each a substituent represented by Formula 2 above;

n, m, o, p, q and r are the same or different and are each independently an integer ranging from 1 to 100;

$L_1$ and $L_2$ are the same or different and are each independently a substituted or unsubstituted alkylene group having 1 to 200 carbon atoms, a substituted or unsubstituted arylene group having 6 to 200 carbon atoms, a substituted or unsubstituted heteroarylene group having 5 to 200 nuclear atoms, or a substituted or unsubstituted cycloalkylene group having 3 to 200 carbon atoms;

$R_1$ to $R_8$ are the same or different and are each independently selected from the group consisting of hydrogen, deuterium, a cyano group, a nitro group, a halogen group, a hydroxyl group, a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 5 to 60 carbon atoms, a substituted or unsubstituted heteroarylalkyl group having 6 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl group having 6 to 30 carbon atoms, and a substituted or unsubstituted aryloxy group having 6 to 30 carbon atoms; and the substituted alkylene group, the substituted arylene group, the substituted heteroarylene group, the substituted cycloalkylene group, the substituted alkyl group, the substituted cycloalkyl group, the substituted alkenyl group, the substituted alkynyl group, the substituted aralkyl group, the substituted aryl group, the substituted heteroaryl group, the substituted heteroarylalkyl group, the substituted alkoxy group, the substituted alkylamino group, the substituted arylamino group, the substituted aralkylamino group, the substituted heteroarylamino group, the substituted alkylsilyl group, the substituted arylsilyl group and the substituted aryloxy group are substituted with one or more substituents selected from the group consisting of hydrogen, deuterium, a cyano group, a nitro group, a halogen group, a hydroxyl group, an alkyl group having 1 to 30 carbon atoms, a cycloalkyl group having 1 to 20 carbon atoms, an alkenyl group having 2 to 30 carbon atoms, an alkynyl group having 2 to 24 carbon atoms, an aralkyl group having 7 to 30 carbon atoms, an aryl group having 6 to 30 carbon atoms, a heteroaryl group having 5 to 60 nuclear atoms, a heteroarylalkyl group having 6 to 30 carbon atoms, an alkoxy group having 1 to 30 carbon atoms, an alkyl amino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms, and an aryloxy group having 6 to 30 carbon atoms, and when they are substituted with a plurality of substituents, these substituents are the same or different.

2. The photocurable composition of claim 1, wherein the UV-curable polyurethane oligomer has a weight-average molecular weight of 10,000 to 1,000,000.

3. The photocurable composition of claim 1, wherein the photoinitiator is a compound represented by the following Formula 3:

[Formula 3]

wherein $X_1$ is S, O or $N(R_{11})$;

$R_9$ to $R_{11}$ are the same or different and are each independently hydrogen, deuterium, a cyano group, a nitro group, a halogen group, a hydroxyl group, a substituted or unsubstituted alkyl group having 1 to 30 carbon atoms, or a substituted or unsubstituted cycloalkyl group having 3 to 30 carbon atoms; and the substituted alkyl group and the substituted cycloalkyl group are substituted with one or more substituents selected from the group consisting of hydrogen, deuterium, a cyano group, a nitro group, a halogen group, a hydroxyl group, an alkyl group having 1 to 30 carbon atoms, a cycloalkyl group having 1 to 20 carbon atoms, an alkenyl group having 2 to 30 carbon atoms, an alkynyl group having 2 to 24 carbon atoms, an aralkyl group having 7 to 30 carbon atoms, an aryl group having 6 to 30 carbon atoms, a heteroaryl group having 5 to 60 nuclear atoms, a heteroarylalkyl group having 6 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms, and an aryloxy group having 6 to 30 carbon atoms, and when they are substituted with a plurality of substituents, these substituents are the same or different.

4. The photocurable composition of claim 1, wherein the oligomer is selected from the group consisting of an epoxy acrylate oligomer, $H_{12}$ Dian-bis-glycidyl ether (4,4'-(1-methylethylidene)biscyclohexanol polymer with (chloromethyl)oxirane), and a mixture thereof.

5. The photocurable composition of claim 1, wherein the stabilizer is selected from the group consisting of 2,6-di-tert-butyl-p-cresol, diethylethanolamine, trihexylamine, a hindered amine, an organic phosphate, a hindered phenol, and mixtures thereof.

6. The photocurable composition of claim 1, wherein an implant is additionally formed in the patient-specific splint or cast in order to prevent the splint or cast from loosening due to changes in the state of the patient's affected area and maintain the ability of the splint or cast to support the patient's affected area.

7. A patient-specific splint or cast produced using 3D printing, the splint or cast comprising the photocurable composition for 3D printing according to claim 1.

* * * * *